US011350881B2

United States Patent
Jauss et al.

(10) Patent No.: US 11,350,881 B2
(45) Date of Patent: Jun. 7, 2022

(54) METHOD FOR SUPPRESSING IMAGE NOISE IN A VIDEO IMAGE STREAM, AND ASSOCIATED MEDICAL IMAGE RECORDING SYSTEM AND COMPUTER PROGRAM PRODUCT

(71) Applicant: Scholly Fiberoptic GmbH, Denzlingen (DE)

(72) Inventors: Joachim Jauss, Rheinhausen (DE); Nicole Giessler, Triberg (DE); Martin Bohning, Herzogsweiler (DE)

(73) Assignee: Scholly Fiberoptic GmbH, Denzlingen (DE)

( * ) Notice: Subject to any disclaimer, the term of this patent is extended or adjusted under 35 U.S.C. 154(b) by 29 days.

(21) Appl. No.: 16/998,055

(22) Filed: Aug. 20, 2020

(65) Prior Publication Data

US 2021/0052226 A1 Feb. 25, 2021

(30) Foreign Application Priority Data

Aug. 22, 2019 (DE) .......................... 102019122667.8

(51) Int. Cl.
*G06T 5/00* (2006.01)
*A61B 5/00* (2006.01)
(Continued)

(52) U.S. Cl.
CPC ............ *A61B 5/7214* (2013.01); *A61B 6/527* (2013.01); *G06T 5/002* (2013.01); *G06T 7/0016* (2013.01); *G06T 2207/20182* (2013.01)

(58) Field of Classification Search
CPC ..... A61B 5/7214; A61B 5/7225; A61B 5/725; A61B 5/7203; A61B 6/527; A61B 6/5264;
(Continued)

(56) References Cited

U.S. PATENT DOCUMENTS

| 4,638,351 A | 1/1987 | Clarke |
| 8,825,138 B2* | 9/2014 | Mistretta ............ G01R 33/4824 600/427 |

(Continued)

FOREIGN PATENT DOCUMENTS

DE 102016205603 10/2017

OTHER PUBLICATIONS

Schoonenberg, G., et al. Adaptive spatial-temporal filtering applied to x-ray fluoroscopy angiography, Medical Imaging 2005, Proc. of SPIE, vol. 5744, pp. 870-877, 2005.

*Primary Examiner* — Jose L Couso
(74) *Attorney, Agent, or Firm* — Volpe Koenig

(57) ABSTRACT

In order to improve the noise suppression in a video image stream 3 of a medical image recording system, the video image stream including a sequence of frames, it is provided that an image processing unit 5 of the image recording system analyses the video image stream 3 continuously in real time and determines at least one variability between successive image pixels of the frames, for example of spatially adjacent image pixels of frames and/or of image pixels of a plurality of the frames corresponding to one another spatially and temporally, in order, on the basis of the variability determined, to set at least one parameter of a noise suppression subsequently applied to the video image stream 3. As a result, the noise suppression can be adapted continuously to a current recording situation.

20 Claims, 1 Drawing Sheet

(51) Int. Cl.
*A61B 6/00* (2006.01)
*G06T 7/00* (2017.01)

(58) Field of Classification Search
CPC . A61B 6/5258; A61B 2576/00; A61B 8/5269;
G06T 7/0016; G06T 7/0012; G06T 7/11;
G06T 7/337; G06T 5/002; G06T 5/10;
G06T 5/20; G06T 5/50; G06T 5/003;
G06T 2207/20182; G06T 2207/20008;
G06T 2207/20012; G06T 2207/10016;
G06T 2207/10056; G06T 2207/10068;
G06T 2207/10048; G06T 2207/10116;
G06T 2207/10132; G06T 2207/20081;
G06T 2207/20084; G06T 2207/30004;
G06T 2207/30048; G06T 2207/10072;
G06T 2207/20032; G06T 2207/20192;
H04N 19/80; H04N 5/144; H04N 5/21;
H04N 9/646; H04N 21/44; G06K 9/40;
G06K 9/36; G06K 9/60; G06K 9/64;
G06K 9/68; G06K 9/70; G06K 9/00744;
G06K 9/2054; G06V 10/20; G06V 10/22;
G06V 10/30; G06V 10/75; G06V 20/46
See application file for complete search history.

(56) References Cited

U.S. PATENT DOCUMENTS

| | | | |
|---|---|---|---|
| 2005/0135698 A1* | 6/2005 | Yatsenko | G06T 5/002 382/260 |
| 2008/0002903 A1* | 1/2008 | Mitchell | G06T 5/002 382/265 |
| 2008/0204600 A1* | 8/2008 | Xu | H04N 5/21 348/607 |
| 2009/0080724 A1* | 3/2009 | Nanbu | G06T 5/50 382/128 |
| 2009/0202129 A1* | 8/2009 | Omi | H04N 5/32 382/132 |
| 2013/0089247 A1* | 4/2013 | Mercuriev | G06T 5/50 382/128 |
| 2014/0153842 A1* | 6/2014 | Pescatore | G06T 5/002 382/264 |
| 2017/0281093 A1 | 10/2017 | Bohm et al. | |
| 2018/0089864 A1* | 3/2018 | Gindele | A61B 6/5258 |
| 2018/0253839 A1* | 9/2018 | Zur | G06T 7/0012 |
| 2019/0043173 A1* | 2/2019 | Keijzers | G06T 5/002 |
| 2019/0340738 A1* | 11/2019 | Hartbauer | G06T 5/002 |
| 2019/0342480 A1* | 11/2019 | Kostrzewa | H04N 5/243 |

* cited by examiner

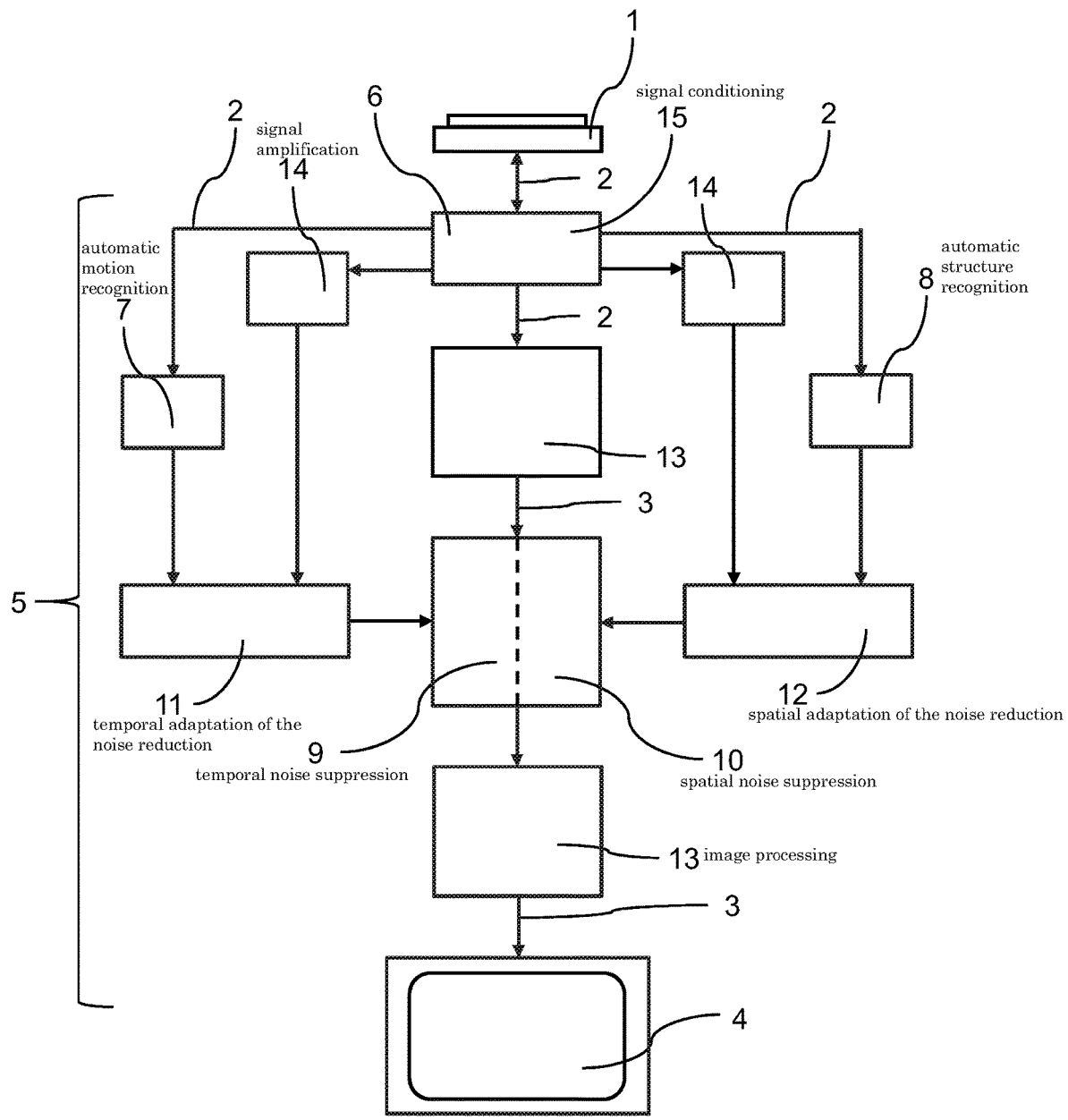

METHOD FOR SUPPRESSING IMAGE NOISE IN A VIDEO IMAGE STREAM, AND ASSOCIATED MEDICAL IMAGE RECORDING SYSTEM AND COMPUTER PROGRAM PRODUCT

INCORPORATION BY REFERENCE

The following documents are incorporated herein by reference as if fully set forth: German Patent Application No. 10 2019 122 667.8, filed Aug. 22, 2019.

TECHNICAL FIELD

The invention relates to a method for suppressing image noise in a video image stream which consists of a sequence of frames and is generated by an image processing unit by processing a signal of an image sensor of a medical image recording system. In this case, each of the frames consists of a number of image pixels and an automated noise suppression reduces image noise in the frames and thus in the video image stream overall.

Such a medical image recording system can be configured for example as a video endoscope or in the form of an exoscope or for example as a digital microscope.

The invention furthermore relates to such a medical image recording system. The latter comprises an image sensor for providing a signal, which can be present in particular in the form of a raw data signal, and an image processing unit for generating a video image stream consisting of a sequence of frames by processing the signal/the raw data signal.

Finally, the invention relates to an associated computer program product which can be loaded into an internal memory of such a medical image recording system and comprises a software code.

BACKGROUND

It is known, for example, that in the case of video endoscopes in typical application situations the video image stream generated is burdened by image noise.

Said image noise is caused by statistical processes in individual pixels from among the pixels of the image sensor of the video endoscope and downstream amplifier circuits and occurs even when the scene is in darkness. Therefore, the image or signal noise is disturbing particularly when the recorded scene has low brightness.

In principle, there is then firstly the possibility of adapting, by way of an automatic exposure control, the shutter speed of the image sensor of the video endoscope and thus the signal strength by virtue of a longer integration time (optical gain), in order to increase the useful signal, that is to say the image information to be recorded, vis-à-vis the constant background noise. The signal-to-noise ratio (SNR) can thus be improved within certain limits, which is advantageous in order to be able to generate high-resolution video images. The SNR can thus be optimized by way of automatic exposure control.

Once the maximum possible shutter speed for a given frame rate of the video image stream, and thus the maximum possible integration time have been reached, an additional amplification of the useful signal can be achieved only by means of an electronic gain. What is disadvantageous about an electronic gain, however, is that the noise in the video image stream is amplified as well, with the result that the signal-to-noise ratio cannot be increased further.

Image noise is influenced by various factors, for example the integration time, the electronic gain, the image processing, the temperature, the exposure situation, etc. Therefore, the image noise varies constantly during operation. Conventional noise reduction methods employ fixed setting parameters, independently of the current noise behavior, but this represents an unsatisfactory compromise in many cases.

Two basic methods are known for suppressing image noise:

In the case of so-called temporal noise suppression, the image data of a plurality of temporally successively recorded images are averaged in order thus to suppress the noise components in the signal. Depending on the degree of recursivity, in this case more or fewer temporally successive images are computationally combined with one another. The degree of recursivity accordingly determines to what extent—from a temporal standpoint—the temporal noise suppression has recourse to image data. What is disadvantageous about temporal noise suppression, however, is that motion artifacts can occur particularly when there are rapidly moving objects within the video images. So-called streaking effects are often observed, for example, wherein rapidly moving image objects in the video image stream are blurred, which is very disturbing for the user of the video endoscope.

In addition, so-called spatial noise suppression methods are known. In the latter, a spatial low-pass filtering is performed only locally within individual sub-domains of a frame of a video stream, that is to say for example within a local image block of a frame, in the case of which filtering the intensities of individual pixels within the respective sub-domain are computationally combined with one another in order thus to suppress the noise components in the signal of this frame. This is typically applied to all the images of a video image stream, thereby suppressing the noise overall in the video image stream. What is disadvantageous about the spatial noise suppression is that often it may offer worse noise suppression and results in a lack of image sharpness compared with a comparable temporal noise suppression.

Furthermore, so-called enhancement algorithms are known for improving the quality of a video image stream. However, they generate additional noise in many application situations since said algorithms are typically based on a signal processing that introduces high frequency components into the useful signal.

SUMMARY

The invention is based on the object of improving previously known methods for suppressing image noise and of making them usable specifically for medical image recording systems such as video endoscopes, for instance.

In order to achieve this object, according to the invention, in the case of a method for suppressing image noise in a video image stream of a medical image recording system as described in the introduction, one or more features described herein are provided. In particular, therefore, according to the invention, in order to achieve the object in a method of the type mentioned in the introduction it is provided that a variability between individual image pixels from among the image pixels is determined continuously and at least one parameter of the noise suppression is set depending on the variability determined.

In other words, the invention thus provides an adaptive noise suppression in a video image stream recorded by an image sensor of a medical image recording system. This adaptation can preferably be effected in real time.

The signal of the image sensor from which a video image stream arises by means of signal processing can be a raw data signal, in particular. Depending on the image sensor used, however, the latter can also already have a dedicated signal processing at the chip level, such that at least one part of said image processing unit is realized on the image sensor. In this case, the signal can also be for example a partly processed signal (pre-processed signal) or even a fully processed video signal.

The determination of variabilities within the meaning of the invention is accomplished efficiently particularly if successive image pixels are compared with one another. Being successive within the meaning of the invention can be understood here both spatially and temporally: the first case can accordingly involve spatially successive image pixels, that is to say in particular spatially adjacent image pixels, of one of said frames. The second case can accordingly involve temporally successive image pixels, that is to say in particular temporally adjacent image pixels, of temporally successive frames from among said frames. In this case, the temporally successive image pixels can preferably correspond to one another spatially, that is to say have for instance the same spatial position (e.g. line/column) in the respective one of said frames.

Accordingly, the variability can be determined by temporally and/or spatially successive image pixels being compared with one another.

In order to implement such an adaptive noise suppression, the sequence of frames can be analyzed continuously by an algorithm, for example, wherein the noise suppression is adapted depending on a variability detected in the frames, that is to say in particular between different frames from among the frames and/or in individual frames from among the frames. This adaptation can concern in particular parameters of the noise suppression and also the type of noise suppression used (spatial and/or temporal).

In the simplest case, a variability within the meaning of the invention can consist in differences in intensity between temporally and/or spatially corresponding pixels of the respective frames. For this purpose, the frames of the video image stream, which are sometimes also referred to as video frames, can be subdivided into sub-domains, in particular into image blocks, for example having a size of 8×4 image pixels.

In the simplest case, the at least one parameter of the noise suppression that is set in the method can be a degree of activity of the respective noise suppression. By way of example, a specific noise suppression, e.g. a temporal noise suppression, can be switched on or off depending on the variability detected.

The at least one parameter can furthermore alternatively or supplementarily also comprise a reduction intensity of the noise suppression, that is to say for example an intensity with which noise in the video image stream is actively damped.

The method according to the invention thus allows a situation-adapted adaptation of the noise reduction intensity and/or of the type of noise suppression used for reducing noise. This is done in each case by automatically adapting at least one parameter of a noise suppression method applied to the video image stream. In this case, this adaptation can be effected in such a way that a noise suppression is set that is currently the highest possible but still does not entail a disturbing loss of image information owing to excessive noise suppression.

The setting or adaptation of the noise suppression can take place in particular continuously during the recording of a video by the image sensor. Furthermore, in this case, the adaptation can react flexibly and automatically to variabilities that arise in the sequence of the frames or in individual frames from among said frames.

As will be able to be explained in even more specific detail, said variabilities can be, in particular, movements of objects or specific image structures that are present or recognizable in the respective frames.

In order to avoid high computational complexity and therefore complex hardware, the setting of the at least one parameter for adapting the noise suppression or the method applied for the noise suppression can be effected for example with the aid of a look-up table, by interpolation or by other mathematical functions known in the prior art.

The adaptive adaptation of the noise suppression additionally makes it possible under changing video recording conditions, that is to say in particular with changing scenes having different proportions of highly detailed structures and/or movements of varying speeds, always to ensure a noise suppression which generates an optimum video image stream for the given image recording system (from the point of view of an observer of the video image stream) with as little noise as possible.

In contrast to conventional methods, in which the noise suppression is adaptable at best by a user in a complex manner during a recording, the method according to the invention relieves the burden on the user of the medical image recording system since the adaptation of the noise suppression proceeds in an automated manner in the background. This is possible since the determination of the variability can take place by an automated image processing of the frames in real time. The hardware required for this can be provided by a medical image recording system that will be described in even more specific detail, in particular by a camera control unit thereof.

The method according to the invention thus implements an intelligent and adaptive noise reduction that adapts automatically to different situations. This solves the frequently occurring problem in practice that the instantaneous noise suppression is often adapted only sub-optimally to the current recording situation: either the noise reduction is too weak, and so noise is visible; or it is too strong, which can give rise to an unsharpness (for example as a result of streaking effects). These known disadvantages are eliminated by the method according to the invention.

According to the invention, the object can also be achieved by further advantageous embodiments as described below and in the claims.

In this regard, the variability can be an, in particular global and/or local, temporal variability. In other words, this type of variability can exist or be detected between temporally directly or indirectly successive entire frames. The type of variability can supplementarily or alternatively also be detected locally for individual corresponding regions between such frames.

For detecting the temporal variability, spatially and/or temporally corresponding image pixels of different frames from among the frames can accordingly be compared with one another. Consequently, the noise suppression whose parameter is set by means of the method according to the invention can be a temporal noise suppression.

In the case of the temporal noise reduction, by way of a motion detector, for example, it is possible to ascertain the extent to which a respective frame changes between two recordings. In other words, the magnitude of the temporal variability between successive images is thus ascertained.

Afterward, the number of images or frames to which the noise suppression is to be applied can then be defined.

With high variability, which may be tantamount to intense motion within the recording situation, it is preferable to perform a low noise reduction in a temporal direction. By contrast, with a low temporal variability, which allows a constant image to be deduced, it is possible to apply a high noise suppression in a temporal direction, that is to say for example using a larger number of successive frames, without relevant information being lost.

In accordance with one preferred configuration, for detecting the temporal variability a motion of at least one object within a temporal sequence of a plurality of the frames can be detected, in particular by means of an automatic motion recognition, that is to say in particular by means of a motion recognition algorithm. In this case, the speed of the detected motion or the extent thereof within a respective frame can be used as a measurement variable that is taken as a basis for the setting of the parameter of the noise suppression.

The at least one parameter that is set depending on the variability determined can be for example a recursivity of a temporal filter, in particular of a temporal low-pass filter. Such an adaptive temporal filter makes it possible to realize a desired adaptive temporal noise suppression which effects temporal filtering to a greater or lesser degree depending on the variability determined. In this case, it is preferable if with increasing temporal variability, that is to say in particular with increasing speed or extent of a motion, the recursivity is reduced. This can be done for example in such a way that a number of frames to which the temporal noise suppression is applied is reduced. This makes it possible to prevent motion artifacts from disturbing the video image stream.

Alternatively, but preferably supplementarily, said variability on the basis of which the at least one parameter is set can also be a spatial variability. The latter can be global, that is to say can be detected for a respective frame in its entirety. It is preferred, however, to use a local variability determined locally for individual sub-domains of a respective frame.

For detecting such a global or local spatial variability spatially closely adjacent image pixels of one of the frames, preferably within sub-domains, for example within image blocks, of in each case one of the frames, can be compared with one another. This comparison can preferably be effected with the aid of an automatic structure recognition, which determines the spatial variability on the basis of image structures, for example edges. Consequently, the noise suppression whose parameter is set can alternatively or supplementarily also be a spatial noise suppression, the latter variant being preferable.

By way of example, a maximum difference between intensity values of the closely adjacent image pixels within a respective sub-domain can be determined as a measure of the spatial variability. This can be realized very simply and nevertheless allows conclusions to be drawn regarding the differentiation of genuine image structures and statistical intensity fluctuations attributable merely to image noise.

In order to make such a differentiation robust, the difference can be compared with a preset or adaptable threshold value. Upon the threshold value being exceeded, the spatial noise suppression for the affected sub-domain can then be correspondingly reduced, that is to say in particular totally deactivated. This makes it possible to prevent important detail structures in the respective frame or the respective sub-domain and thus respectively in the video stream from being lost as a result of an excessive spatial noise suppression. In this case, the exceedance of the threshold value is interpreted in the method such that the intensity differences involve relevant image structures which are intended to be incorporated into the video image stream with only weak filtering or no filtering at all.

In one possible configuration of the method, the frames of the video image stream are divided into sub-domains, for example rectangular blocks of 8×4 image pixels, wherein within a block a check is made to establish whether the spatial variability, which can be described for example by a maximum difference between intensity values of individual image pixels from among the image pixels, exceeds a threshold value. If this is the case, then a structure that is not attributable to noise is deduced, and the spatial filter is accordingly not applied, in order not to adversely affect the image information here. By contrast, if the difference lies below the threshold value, that is to say if the spatial variability lies below a specific threshold, then it is assumed that the variability is merely attributable to noise and the spatial image filter is accordingly applied, in order to reduce the image noise within this sub-domain. The image filter can be configured for example as a spatial low-pass filter having a frequency response that has been previously optimized under test conditions.

Due to varying lighting situations, for example, the required electronic gain of the signal of the image sensor of the medical image recording system can fluctuate during a video recording, which affects the absolute level of the image noise. In order to take account of this factor, the invention provides choosing the threshold value depending on an instantaneous, in particular electronic, gain factor with which the signal is amplified, in particular in an automated manner.

In this case, the threshold value can preferably be chosen to be all the higher, the higher the instantaneous gain factor is set. This is because the higher the instantaneous gain factor, the higher the respective noise turns out to be, too, such that the threshold value could easily be surpassed by noisy image pixels without adaptation, which would result in an incorrect interpretation without adaptation of the threshold value.

Following a similar train of thought it may be advisable to choose the threshold value to be all the higher, the higher actual instantaneous noise turns out to be. Therefore, alternatively or supplementarily to said instantaneous gain factor, the threshold value can also be chosen depending on instantaneous noise, in particular depending on an instantaneous noise intensity (e.g. measured in dB).

In accordance with one particularly preferred configuration of the method according to the invention, in this case the instantaneous noise/instantaneous noise intensity can be ascertained, that is to say in particular calculated, from covered pixels of the image sensor, which cannot detect incident light. For this purpose, said covered pixels can be read separately.

In some image sensors, covered pixels of this type are positioned at the edge of an array of non-covered light-sensitive pixels that is provided for the actual image recording; they are typically realized monolithically with the light-sensitive pixels and therefore exposed to the same influencing factors, for instance the same temperature, as the light-sensitive pixels that supply the actual image sensor signal. Therefore, such covered pixels can supply a statistical estimated value for the noise component, which is present at the input of an amplifier circuit used for amplifying the (image) signal of the image sensor since these light-insensitive pixels also have thermal noise, for example. Consequently, reading covered pixels enables the noise suppression to be regulated very precisely in real time, depending on an instantaneous noise behavior of the image sensor. A variety of factors that influence the image noise can be taken into account as a result.

Furthermore, with the aid of such covered pixels, which some image sensors already have nowadays, an instantaneous noise factor can also be estimated, which can be ascertained for example as a logarithm of a ratio between an SNR at the input and an SNR at the output of said amplifier circuit. Such a noise factor ascertained with the aid of the instantaneous noise can also be used in an equivalent way in order to adapt the threshold value accordingly.

In principle, there is no interaction at all between temporal and spatial noise suppression. It can be stated, however, that in many typical applications, for instance in video endoscopy, a temporal noise suppression is more powerful than a spatial noise suppression.

According to the invention, therefore, precisely in video endoscopy applications, it may be advantageous to configure both the temporal noise suppression and the spatial noise suppression depending on the instantaneously used electronic gain.

Furthermore, it should be taken into account that, depending on the design of the system, the image noise has a characteristic spectrum that is substantially constant. Even when the noise is amplified, this frequency spectrum generally does not change significantly. Therefore, the low-pass filter used for filtering can be optimally tuned to the noise behavior of the optical system under laboratory conditions and this filter characteristic can then be maintained even for different gains.

In accordance with the previous explanations, therefore, alternatively or supplementarily to the temporal recursivity explained above, the at least one parameter that is set depending on the variability respectively determined can also be a characteristic of an adaptive spatial image filter, in particular of an adaptive spatial low-pass filter, for example a cut-off frequency or a signal damping of the low-pass filter. If digital filters are used, for example, such an adaptation is possible in real time. Such an adaptive spatial low-pass filter can be applied to the above-explained sub-domains, in particular the above-explained image blocks, of the frames in order to realize an adaptive spatial noise suppression.

Alternatively or supplementarily, however, provision can also be made for a non-adaptive spatial low-pass filtering with a preset characteristic, that is to say in particular a non-adaptive spatial low-pass filter, to be used in the method. This can be applied, that is to say in particular digitally applied, or not actually applied to the sub-domains, in particular the image blocks, depending on the spatial variability determined. By this means, too, it is possible to realize an adaptive spatial noise suppression within the meaning of the invention. In this case, preferably, the non-adaptive low-pass filtering can be applied upon the threshold value explained above being undershot, and not be applied upon the threshold value being exceeded. For in this way it is possible, in a targeted manner, to suppress the image noise and at the same time to protect relevant image structures.

In accordance with one particularly preferred variant of the method, which offers a noise suppression that is optimized in each case for a wide variety of image scenarios, a temporal noise suppression as explained above and a spatial noise suppression likewise as explained above can be applied to respective frames from among the frames in parallel and/or simultaneously. It is thus possible to output a corrected image video stream with an improved signal-to-noise ratio, specifically in a wide variety of recording scenarios with changing proportions of image structures and motion in the images.

In the case of this configuration, it is preferable if with low or decreasing temporal variability in the frames, a degree of activation of the temporal noise suppression has been or is increased. This is because this use of the temporal noise suppression enables an optimum noise suppression taking account of an instantaneous image situation. By contrast, a degree of activation of the spatial noise suppression can be chosen independently of the temporal variability in this case.

Supplementarily, provision can furthermore be made for a recursivity of the temporal noise suppression, in particular a recursivity of a or of said temporal filter, which can be configured in particular as a temporal low-pass filter, to be chosen or adapted depending on an, in particular on the above-explained electronic, instantaneous gain factor with which the signal of the image sensor is amplified. In this case, it is advantageous for an optimum noise suppression if the recursivity is increased with increasing gain factor.

Alternatively or supplementarily thereto, a characteristic of the spatial noise suppression can also be chosen or adapted in an analogous way, that is to say depending on an, in particular on the above-explained electronic, instantaneous gain factor. This characteristic can be in particular a characteristic of a, in particular of the above-explained, spatial low-pass filter.

Both said recursivity and said characteristic can furthermore alternatively be chosen or adapted depending on the noise factor already explained above in a different context.

As was mentioned in the introduction, the at least one parameter can be set with the aid of a look-up table, specifically in particular to values previously optimized for different variabilities. What is advantageous about the use of such a look-up table is that there is no need to carry out a complex calculation of an instantaneously optimum value for the at least one parameter in real time. As a result, hardware required for such computationally intensive tasks, such as an FPGA, for example, can be dispensed with.

In order to achieve the stated object, one or more features provided herein directed to a medical image recording system are furthermore provided. In particular, therefore, according to the invention, in order to achieve the object in the case of a medical image recording system of the type described in the introduction, which can additionally comprise a display unit for visualizing the video image stream, it is provided that the image processing unit of the medical image recording system is configured to determine a variability between successive image pixels, that is to say in particular a temporal variability between corresponding image pixels of a plurality of the frames and/or a spatial variability between adjacent image pixels within a respective one of the frames, and, depending on the respective variability determined, to set at least one parameter of an automated noise suppression that enables image noise in the video image stream to be suppressed or suppresses it during the operation of the image recording system.

In accordance with one preferred configuration, in this case, said image processing unit, which can also consist of a plurality of components, can be located, at least partly, in a camera control unit of the image recording system.

In other words, the image processing unit of the medical image recording system can thus be configured continuously to analyze the sequence of frames and to adapt the noise suppression depending on a variability detected in the frames, that is to say in particular between different frames from among the frames and/or in individual frames from among the frames, in particular in sub-domains of individual frames from among the frames. This adaptation, which is preferably performed by the image recording system in real time, can be effected automatically, for example by setting at least one parameter that influences the noise suppression applied to the video image stream.

It should be declared right away here that it is particularly expedient if the medical image recording system described above is configured or comprises means configured to implement one of the methods according to the invention— already described above—for suppressing image noise in the video image stream. Consequently, in particular, the image processing unit can be configured for carrying out one of the methods explained above, that is to say in particular as claimed in any one of the claims directed to a method.

For recognizing a motion of at least one object within the video image stream, the image processing unit can comprise a motion detector. Said motion detector can implement for example a motion recognition algorithm based on an image processing of the signal of the image sensor.

Furthermore, the image processing unit can supplementarily or alternatively comprise an image structure recognition module for determining a local spatial variability on the basis of image structures, in particular in sub-domains, that is to say e.g. image blocks, of the frames.

Both the motion detector and the image structure recognition module, for the respective recognition, can have recourse to the original signal of the image sensor or else to a partly processed signal or a fully processed video signal.

For the detection of spatial variability in the frames, the image processing unit can furthermore be configured to detect intensity differences between image pixels within sub-domains, in particular within image blocks, of the respective frames of the video image stream and to compare them with a threshold value. In this case, said threshold value can be stored or be settable, as has already been explained further above. In the case of such a configuration, it is preferable if the image processing unit is configured, depending on the result of this comparison, to adapt a low-pass filtering of the respective sub-domain, that is to say in particular to attenuate the low-pass filtering, or to interrupt the low-pass filtering entirely.

Finally, in order to achieve the stated object, according to the invention, one or more features described herein directed to a computer program product are provided. In particular, therefore, according to the invention, in order to achieve the object in the case of a computer program product of the type described in the introduction, it is provided that the computer program product comprises a software code with the aid of which one of the above-described methods according to the invention for suppressing image noise can be carried out when the software code is executed by a controller of a medical image recording system.

The computer program product can preferably be configured in such a way that it can be loaded into an internal memory of a medical image recording system according to the invention as explained above. Moreover, it may be necessary for the software code to be adapted to the respective controller of the medical image recording system.

BRIEF DESCRIPTION OF THE DRAWINGS

The invention will now be described in greater detail on the basis of exemplary embodiments, but is not restricted to these exemplary embodiments. Further exemplary embodiments result from combination of the features of individual or a plurality of claims among one another and/or with individual or a plurality of features of the respective exemplary embodiment. In particular, embodiments of the invention can thus be obtained from the following description of a preferred exemplary embodiment in conjunction with the general description, the claims and the drawings.

The sole FIGURE shows a schematic illustration of the flow of information between individual components of an image recording system according to the invention when a method according to the invention for suppressing image noise is applied to a video image stream generated by the image recording system.

DETAILED DESCRIPTION

The sole FIGURE schematically shows a flow of information proceeding from an image sensor 1 of a medical image recording system in the form of a video endoscopy system.

The image sensor 1 generates a signal 2, from which, by a complex image processing unit 5 comprising a plurality of components and signal paths, a video image stream 3 consisting of a sequence of frames is generated. The video image stream 3 is then ultimately displayed on a monitor 4.

An automatic lighting control 6 firstly sets the optical gain by varying a shutter speed for the image sensor 1 and thereby optimizes as much as possible the signal-to-noise ratio (SNR) in the signal 2 output by the image sensor 1. To that end, the automatic lighting control 6 on the one hand transmits control signals to the image sensor 1; on the other hand, it receives and processes continuously the signal 2 emitted by the image sensor 1.

The automatic lighting control 6 additionally controls the instantaneously used electronic gain factor of a respective signal amplification 14 that electronically amplifies the signal 2. At the same time a signal conditioning 15 of the signal 2 (signal preprocessing) also takes place in this system block.

The instantaneously set electronic gain factor is also forwarded by the respective signal amplification 14 to a unit for the temporal adaptation of the noise reduction 11 (temporal SNR adaptation) and to a unit for the spatial adaptation of the noise reduction 12 (spatial SNR adaptation).

These two units 11, 12 additionally each receive regulation signals from an automatic motion recognition 7 and, respectively, from an automatic structure recognition 8 (cf. the signal paths in the sole FIGURE), with the aid of which respectively motions and image structures are detected in the sequence of frames.

For this purpose, the automatic motion recognition 7, which is embodied as a motion detector, and also the automatic structure recognition 8, which is configured as an image structure recognition module, each process a partly processed signal obtained by the signal conditioning 15 of the signal 2 of the image sensor 1. In further configurations, it is also conceivable for the motion recognition 7 and/or the structure recognition 8 for the same purpose directly to access the signal 2 or else the video image data stream 3 output by the image processing block 13 (also referred to as picture processing).

The units 11 and 12 thus each detect variabilities, namely motions and image structures, respectively, in the sequence of frames and accordingly set at least one parameter of a temporal noise suppression 9 and of a spatial noise suppression 10 respectively.

In this case, the respective detection of the variability is effected by analysis of the intensities of individual image pixels of the frames and—in the case of the motion recognition—with the aid of a specific motion recognition algorithm.

As illustrated by the dashed line in the FIGURE, both of these noise suppressions 9, 10 are applied to a video image stream 3 that is output on the basis of a first image processing 13 (picture processing) of the signal 2.

In this case, depending on a motion detected by the automatic motion recognition 7 and/or depending on an image structure detected by the automatic structure recognition 8, a degree of activation of the temporal noise suppression 9 can be increased. As a result, the noise suppression can thereby be manifested with more or less temporal character and/or more or less spatial character, which shows the adaptivity of the noise suppression.

In this case, with only little detected motion, the degree of activation of the temporal noise suppression is increased, such that the latter can be used optimally for noise suppression. By contrast, the degree of activity of the spatial noise suppression can be chosen independently of the detected motion in the video image data stream 3, for example depending on image structures recognized locally in image segments of the frames.

The respective degree of activity of the two noise suppression paths illustrated in sole FIGURE (left and right halves, respectively, of the image processing unit 5 illustrated) thus depends on the variabilities respectively detected in the video image stream 3. As a result, the noise suppression provided by the image processing unit 5 overall is automatically adapted to the respective recording situation and thus always provides an optimized type of noise suppression.

As a result, the video image stream 3 transmitted to the monitor 4, said video image stream being generated by a further image processing unit 13 (final picture processing), thus always has the best possible SNR for the video endoscopy system since the image processing unit 5 adaptively adapts the noise suppression to different image scenarios, without the user of the video endoscopy system having to intervene for this purpose.

In summary, in order to improve the noise suppression in a video image stream 3 of a medical image recording system, said video image stream consisting of a sequence of frames, it is provided that an image processing unit 5 of the image recording system analyses the video image stream 3 continuously in real time and determines at least one variability between successive image pixels of the frames, for example of spatially adjacent image pixels of frames and/or of image pixels of a plurality of the frames corresponding to one another spatially and temporally, in order, on the basis of the variability determined, to set at least one parameter of a noise suppression subsequently applied to the video image stream 3. As a result, the noise suppression can be adapted continuously to a current recording situation.

LIST OF REFERENCE SIGNS

1 image sensor
2 signal (supplied by 1)
3 video image stream
4 monitor
5 image processing unit
6 automatic lighting control
7 automatic motion recognition
8 automatic structure recognition
9 temporal noise suppression
10 spatial noise suppression
11 temporal adaptation of the noise reduction
12 spatial adaptation of the noise reduction
13 image processing
14 signal amplification
15 signal conditioning

The invention claimed is:

1. A method for suppressing image noise in a video image stream (3) which includes a sequence of frames and is generated by an image processing unit (5) by processing a signal (2) of an image sensor (1) of a medical image recording system, namely a videoendoscope or exoscope or digital microscope, wherein each of the frames consists of a number of image pixels, the method comprising:
   using an automated noise suppression to reduce image noise in the frames and thus in the video image stream (3) overall, and
   continuously determining a variability between individual image pixels from among the image pixels and
   setting at least one parameter of the noise suppression depending on the variability that is determined, wherein the noise suppression is adapted in real time
   by adapting a recursivity of a temporal noise suppression
   and/or
   by reducing or deactivating a spatial noise suppression.

2. The method as claimed in claim 1, further comprising determining the variability by comparing at least one of temporally or spatially successive image pixels with one another.

3. The method as claimed in claim 1, wherein the noise suppression is a temporal noise suppression (9).

4. The method as claimed in claim 1, wherein the variability is at least one of a global or local temporal variability, and for detecting the temporal variability, the method further comprises comparing at least one of spatially or temporally corresponding image pixels of different frames from among the frames with one another.

5. The method as claimed in claim 4, further comprising for detecting the temporal variability a motion of at least one object within a temporal sequence of a plurality of the frames is detected using an automatic motion recognition (7).

6. The method as claimed in claim 5, wherein the at least one parameter is a recursivity of a temporal filter, and with increasing temporal variability, the recursivity is reduced such that a number of frames to which the temporal noise suppression is applied is reduced.

7. The method as claimed in claim 1, wherein the noise suppression is a spatial noise suppression.

8. The method as claimed in claim 1, wherein the variability is a spatial variability, and for detecting the spatial variability the method further comprises comparing spatially closely adjacent image pixels of one of the frames with one another using an automatic structure recognition (8), which determines the spatial variability based on image structures.

9. The method as claimed in claim 8, wherein a maximum difference between intensity values of the closely adjacent image pixels within a respective sub-domain is determined as a measure of the spatial variability.

10. The method as claimed in claim 9, wherein the difference is compared with a preset or adaptable threshold value and, in the event of the threshold value being exceeded, the spatial noise suppression for the affected sub-domain is reduced or deactivated.

11. The method as claimed in claim 10, further comprising choosing the threshold value depending on an instantaneous gain factor with which a signal is amplified, and the threshold value is chosen to be higher, the higher the instantaneous gain factor is set, or the threshold value is chosen depending on an instantaneous noise factor.

12. The method as claimed in claim 11, wherein the at least one parameter is alternatively or supplementarily a characteristic of an adaptive spatial image filter, and the image filter is applied to sub-domains of the frames in order to realize an adaptive spatial noise suppression.

13. The method as claimed in claim 11, further comprising applying a non-adaptive spatial low-pass filtering with a preset characteristic depending on the spatial variability determined to sub-domains of the frames, and the non-adaptive low-pass filtering is applied in the event of the threshold value being undershot and is not applied in the event of the threshold value being exceeded.

14. The method as claimed in claim 2, further comprising applying a temporal noise suppression and a spatial noise suppression to respective ones of the frames from among the frames at least one of in parallel or simultaneously, such that a corrected image video stream with an improved signal-to-noise ratio is outputable, and with low or decreasing temporal variability in the frames, a degree of activation of the temporal noise suppression is increased.

15. The method as claimed in claim 14, further comprising selecting a recursivity of the temporal noise suppression in each case depending on an instantaneous gain factor with which the signal is amplified, or depending on instantaneous noise, increasing the recursivity with at least one of increasing gain factor or with increasing noise, and the at least one parameter is set using a look-up table, to values previously optimized for different variabilities.

16. The method as claimed in claim 15, further comprising ascertaining the instantaneous noise from covered ones of the pixels of the image sensor, which cannot detect incident light.

17. A medical image recording system, namely a videoendoscope or exoscope or digital microscope, comprising an image sensor for providing a signal and an image processing unit for generating a video image stream consisting of a sequence of frames by processing the signal, the image processing unit includes a controller that is configured to determine at least one of a temporal, a spatial, or a temporal and spatial variability between successive image pixels of a plurality of the frames, or a spatial variability between adjacent image pixels within a respective one of the frames, and, depending on the respective variability determined, is configured to set at least one parameter of an automated noise suppression that enables image noise in the video image stream to be suppressed, wherein the noise suppression is adapted in real time
    by adapting a recursivity of a temporal noise suppression and/or
    by reducing or deactivating a spatial noise suppression.

18. The image recording system as claimed in claim 17, wherein the image processing unit comprises at least one of a motion detector for recognizing a motion of at least one object within the video image stream or an image structure recognition module for determining a local spatial variability on the basis of image structures of the frames.

19. The image recording system as claimed in claim 17, wherein the image processing unit is configured to detect intensity differences between image pixels within sub-domains of the respective frames of the video image stream and to compare said intensity differences with a threshold value, and depending on a result of this comparison, to adapt a low-pass filtering of the respective sub-domain.

20. A non-transitory computer readable medium, having stored thereon, instructions that when executed by a controller of a medical image recording system, namely a videoendoscope or exoscope or digital microscope, cause the medical image recording system to perform operations for suppressing image noise in a video image stream (3) which includes a sequence of frames and is generated by an image processing unit (5) by processing a signal (2) of an image sensor (1) of the medical image recording system, wherein each of the frames consists of a number of image pixels; and the operations comprise
    using an automated noise suppression to reduce image noise in the frames and thus in the video image stream (3) overall;
    continuously determining a variability between individual image pixels from among the image pixels
    determining the variability by comparing at least one of temporally or spatially successive image pixels with one another and
    setting at least one parameter of the noise suppression depending on the variability that is determined, wherein the noise suppression is adapted in real time
    by adapting a recursivity of a temporal noise suppression and/or
    by reducing or deactivating a spatial noise suppression.

* * * * *